United States Patent [19]

Irick, Jr. et al.

[11] 3,988,295

[45] Oct. 26, 1976

[54] ORGANIC COMPOSITIONS STABILIZED WITH BENZOXAZOLE OR OXADIAZOLE COMPOUNDS

[75] Inventors: Gether Irick, Jr.; Charles A. Kelly, both of Kingsport; James C. Martin, Johnson City, all of Tenn.

[73] Assignee: Eastman Kodak Company, Rochester, N.Y.

[22] Filed: July 1, 1974

[21] Appl. No.: 484,723

Related U.S. Application Data

[62] Division of Ser. No. 298,040, Oct. 16, 1972, Pat. No. 3,864,354.

[52] U.S. Cl. .................. 260/45.8 NZ; 106/176; 260/240 D; 260/240.9; 260/307 G
[51] Int. Cl.² ..................................... C08K 5/00
[58] Field of Search ........ 260/45.8 NZ, 307, 240 D, 260/240.9; 106/176, 45.95 F

[56] References Cited

UNITED STATES PATENTS

| | | | |
|---|---|---|---|
| 3,247,160 | 4/1966 | Anderson | 260/45.8 NZ |
| 3,412,089 | 11/1968 | Ohkawa | 260/240 |
| 3,586,673 | 6/1971 | Bloom | 260/45.8 NZ |

*Primary Examiner*—Donald E. Czaja
*Assistant Examiner*—William E. Parker
*Attorney, Agent, or Firm*—Clyde L. Tootle; Daniel B. Reece, III

[57] ABSTRACT

Benzoxazole or oxadiazole type compounds chemically combined with certain hydroxyaryl type compounds give greatly and unexpectedly improved ultraviolet stabilization to polymeric materials at concentrations ranging from about 0.05 to about 5.0 percent by weight, preferably from about 0.1 to about 2.0 percent by weight of the polymer being stabilized. These stabilizers are effective in the presence of other additives commonly employed in polymeric compositions including pigments, colorants, fillers, reinforcing agents and the like. These stabilizers may be incorporated into the polymer melt, dissolved in the polymer dope, or coated on the exterior of the molded article, film or extruded fiber.

11 Claims, No Drawings

ORGANIC COMPOSITIONS STABILIZED WITH BENZOXAZOLE OR OXADIAZOLE COMPOUNDS

This is a division of application Ser. No. 298,040 filed Oct. 16, 1972 now U.S. Pat. No. 3,864,354.

This invention concerns novel, ultraviolet stabilizers which are unusually effective for stabilizing various synthetic polymers.

Ultraviolet stabilizers commonly used to protect such polymers as polyesters, polyamides, polyolefins, ABS plastics, polystyrene, poly(vinyl chloride) and cellulose esters from the deleterious effects of solar irradiation, typically include the 2-hydroxybenzophenones (typified by I) and the 2-hydroxybenzotriazoles (typified by II).

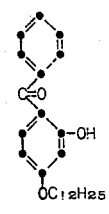
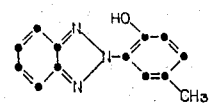

I  II

It will be seen hereinafter that these compounds are not nearly as effective stabilizers as the compounds of the present invention, nor are they retained in the polymeric composition to such a high degree as the present stabilizers, particularly in thin sections such as in powder coatings.

An object therefore of the present invention is to provide more effective and permanent ultraviolet stabilizers for polymeric composition. This and other objects hereinafter appearing have been obtained in accordance with the present invention through the discovery that benzoxazole or oxadiazole type compounds chemically combined with certain hydroxyaryl type compounds give greatly and unexpectedly improved ultraviolet stabilization to polymeric materials at concentrations ranging from about 0.05 to about 5.0 percent by weight, preferably from about 0.1 to about 2.0 percent by weight of the polymer being stabilized. These stabilizers are effective in the presence of other additives commonly employed in polymeric compositions including pigments, colorants, fillers, reinforcing agents and the like. These stabilizers may be incorporated into the polymer melt, dissolved in the polymer dope, or coated on the exterior of the molded article, film or extruded fiber.

The new stabilizers of this invention consist of segments A and B or A and C wherein segment A is of the structure:

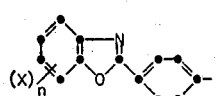
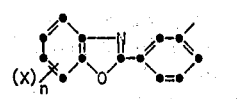

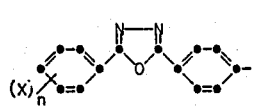
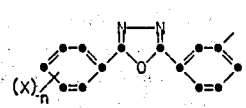

wherein X is meta or para to the heterocyclic ring and may be the following: $C_6H_5$, Cl, Br, lower alkyl and CN, where $n = 0-3$; segment B is of the structure:

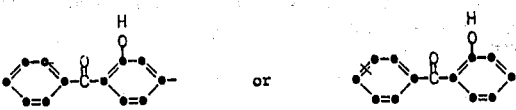

wherein the radical bond is either meta or para to the carbonyl group, A and B being linked through a group selected from

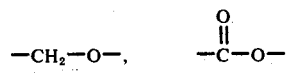

and —O—; and segment C is of the structure

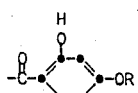

wherein R is

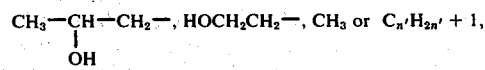

wherein $n' = 2$–18, A and C being linked through a carbon-carbon bond. The resulting series of compounds is as follows:

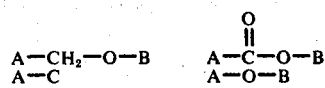

Examples 1 and 5 below employ the following general method for producing compounds of the type A—CH₂OB:

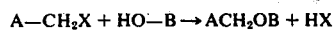

X = halogen
A base is used, in this case potassium carbonate, to accept the HX.

Example 2 employs the following general method for producing compounds of the type

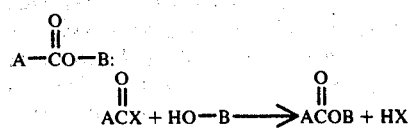

X = halogen
A base is used, in this case sodium hydroxide, to accept the HX.

Examples 3 and 4 employ the following general method for synthesizing compounds of the type A—C.

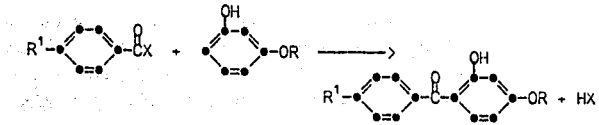

X = halogen

Type A—O—B, may be prepared as follows by the Ullman reaction:

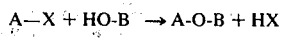

X = halogen

EXAMPLE 1

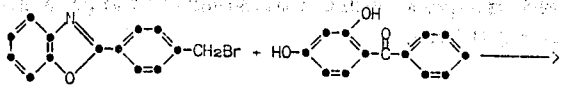

α-(4-benzoyl-3-hydroxyphenoxy)2-p-tolylbenzoxazole

To a solution of 21.4 g. (0.1 mole) of 2,4-dihydroxybenzophenone and 28.8 g. (0.1 mole) of 2-(α-bromo-p-tolyl) benzoxazole in 300 ml. of 2-butanone, is added 100 g. of potassium carbonate. The mixture is placed in a 3-necked reaction flask equipped with a mechanical stirrer and reflux condenser. The mixture is refluxed for 16 hr., cooled to room temperature and combined with 1000 ml. of ice water. The precipitated solid product is collected by filtration and washed with water. The crude product is recrystallized from 2-butanone, giving 33.0 g. of an off-white solid, m.p. 184°–85° C. (80% yield). The structure and purity of the product are confirmed by NMR and elemental analysis.

Preparation of the above benzoxazole reactant is as follows: o-aminophenol is reacted with p-toluic acid to yield 2-(p-tolyl)benzoxazole; this intermediate is then brominated with N-bromosuccinimide to obtain 2-4-bromomethylphenyl)-benzoxazole.

EXAMPLE 2

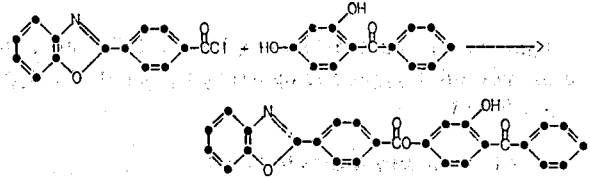

4-Benzoyl-3-hydroxyphenyl-p-(2-benzoxazolyl)benzoate

To a solution of 21.4 g. (0.1 mole) of 2,4-dihydroxybenzophenone in 150 ml. of water, containing 4.0 g. (0.1 mole) of sodium hydroxide, is added dropwise a solution of 25.7 g. (0.1 mole) of 4-(2-benzoxazolyl)-benzoyl chloride in 400 ml. of chloroform. The reaction mixture is stirred vigorously and heated at reflux for 4 hr. after the addition is complete. The mixture is cooled to room temperature, the organic layer is separated, washed with warm water and filtered through filter-cel. The solvent is evaporated on a steam bath giving 38 g. of a light yellow solid (90% crude yield). The crude product is recrystallized from toluene (2X) to give 29 g. of an almost white solid, m.p. 191°–192° C. (68% yield). The structure and purity of the product are confirmed by NMR and elemental analysis.

The above benzoxazolyl reactant was prepared as follows: 2-(p-tolyl) benzoxazole was oxidized with air over a suitable catalyst bed to yield 4-(2-benzoxazolyl)-benzoic acid. This acid was converted to the acid chloride by reaction with thionyl chloride.

EXAMPLE 3

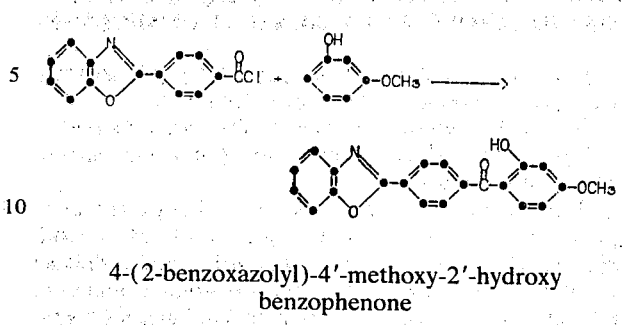

4-(2-benzoxazolyl)-4'-methoxy-2'-hydroxy benzophenone

To a stirred solution of 12.8 g. (0.05 mole) of 4-(2-benzoxazolyl)benzoyl chloride in 200 ml. of 1,2-dichloroethane is added, in small increments, 14.8 g. (0.11 mole) of anhydrous aluminum chloride at room temperature. The resulting solution is cooled to 10° C. and a solution of 6.2 g. (0.05 mole) of m-methoxyphenol in 50 ml. of dichloroethane is added dropwise over a period of 10 min. The reaction mixture is stirred at 10° C. for 30 min., then allowed to warm to room temperature and stirred at reflux for 1 hr. The reaction mixture is cooled to room temperature and combined with 300 g. cracked ice containing 50 ml. of concentrated hydrochloric acid. The organic layer is separated and washed 2 times with warm water. The organic layer is filtered through filter-cel and the solvent is evaporated on a steam bath leaving a yellow solid residue. The crude solid product is recrystallized from toluene to give 10 g. yellow crystals, m.p. 177°–179° C. (61% yield). The structure and purity of the product are confirmed by IR, NMR, and elemental analysis.

In examples 4 and 5 below, the oxidazole reactant was obtained from the mixed hydrazide

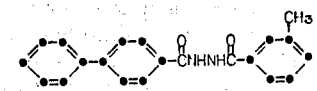

which was cyclized to yield 2-biphenylyl-5-(m-tolyl)-1,3,4-oxadiazole. This intermediate was then air-oxidized over a catalyst bed to the carboxylic acid. This was converted to the acid chloride of Example 4 by reaction with thionyl chloride. In Example 5, the intermediate was brominated with N-bromosuccinimide to yield the bromomethyl reactant.

EXAMPLE 4

3-(5-p-Biphenylyl-1,3,4-oxadiazol-2-yl)-2'-hydroxy-4'-methoxybenzophenone

To a stirred solution of 10 g. (0.08 mole) m-methoxyphenol in 100 ml. 1,2-dichloroethane, containing 13.3 g (0.1 mole) of anhydrous aluminum chloride is added dropwise a solution of 18 g. (0.05 mole) 2-biphenylyl-5-m(chlorocarbonyl)phenyl-1,3,4-oxadiazole in 400 ml. 1,2-dichloroethane at ambient temperature. The resulting solution is heated at boiling for 4 hr., cooled to 40° C. and poured into 500 ml. ice water containing 50 ml. concentrated hydrochloric acid. After standing overnight, the top layer is decanted from the organic layer. The solvent layer is washed several times with water and dried over sodium sulfate.

The solvent is evaporated on the steam bath, giving a light yellow solid. The crude product is treated with Darco G-60 from toluene to yield 21 g. (91%) of a white solid, m.p. 197°–198° C. The structure and purity of the product are confirmed by NMR and elemental analysis.

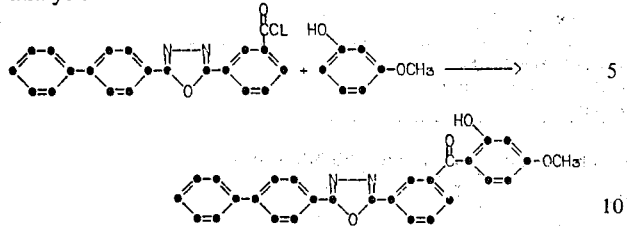

EXAMPLE 5

4-{[m-(5-p-Biphenylyl-1,3,4-oxadiazol-2-yl)benzyl-]oxy}-2-hydroxybenzophenone

To a solution of 11 g. (0.05 mole) 2,4-dihydroxybenzophenone and 20 g. (0.05 mole) 2-biphenyl-5-[3-(bromomethyl)phenyl]-1,3,4-oxadiazole in 300 ml. 2-butanone is added 50 g. anhydrous potassium carbonate. The mixture is placed in a 3-necked reaction flask, equipped with a mechanical stirrer and reflux condenser, and heated at reflux for 8 hr. The reaction mixture is cooled to 40°C. and combined with 500 ml. cold water. The product separates as a gum. The liquid is decanted and the crude product treated with Darco G-60 from benzene.

The yield is 12.5 g. (49%) of an off-white solid, m.p. 177°–179° C. The structure and purity of the product are established by NMR and elemental analysis.

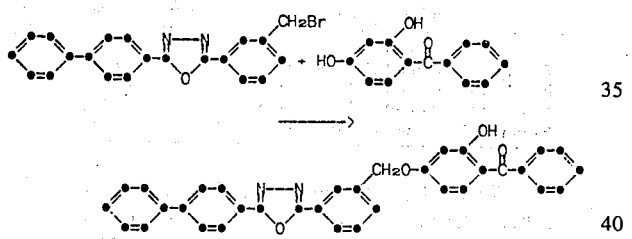

Other specific compounds coming within the present invention are as follows:

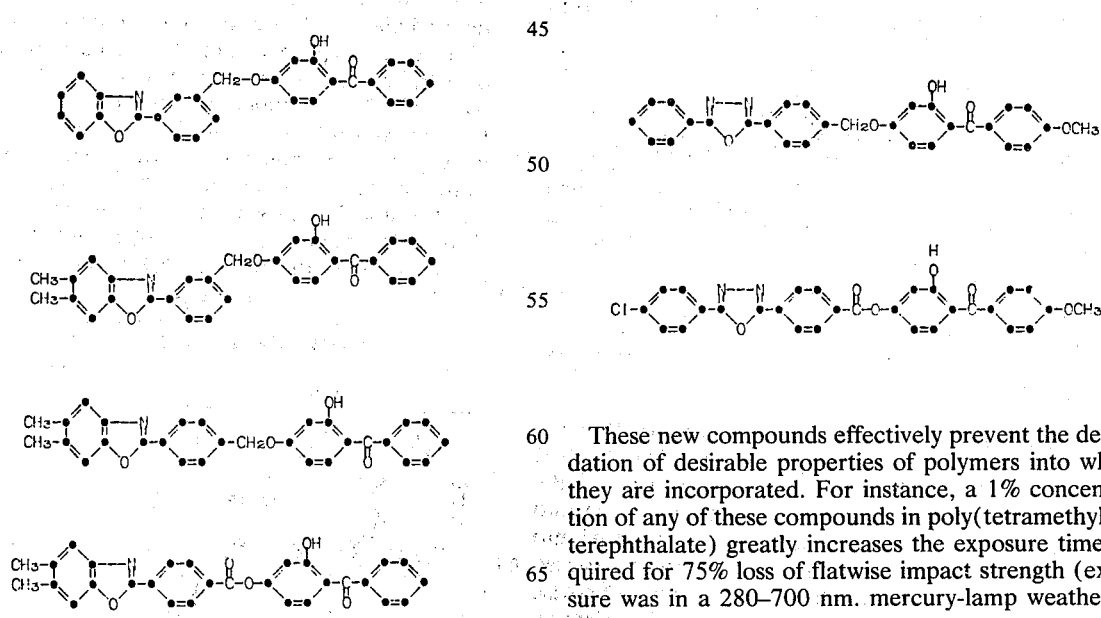

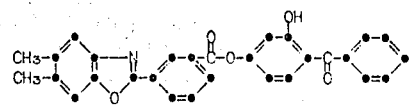

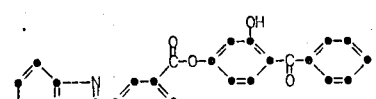

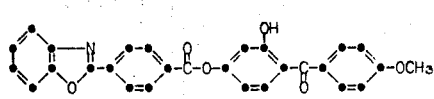

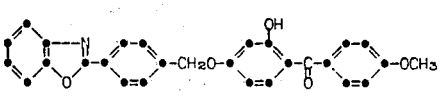

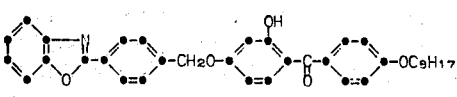

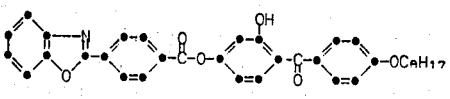

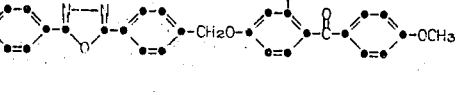

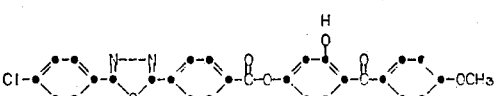

These new compounds effectively prevent the degradation of desirable properties of polymers into which they are incorporated. For instance, a 1% concentration of any of these compounds in poly(tetramethylene terephthalate) greatly increases the exposure time required for 75% loss of flatwise impact strength (exposure was in a 280–700 nm. mercury-lamp weathering device) relative to the neat polymer as shown in Table I below.

Table I

Weathering Data for Stabilizers in 10-mil Cellulose Acetate Butyrate (13.1% Acetyl, 36.5% Butyryl) Films Exposed To A Fluorescent Mercury Lamp

| Compound of Examples | Concentration % by Weight | Time-to-Embrittlement (Hr.) |
| --- | --- | --- |
| 1 | (0.5) | 584 |
|  | (1.0) | 1150 |
| 2 | (0.5) | 466 |
| 3 | (0.5) | 512 |
| 4 | (0.5) | >500 |
| 5 | (0.5) | >500 |
| Control (No Stabilizer) |  | 220 |
| [structure: 2-hydroxy-4-dodecyloxybenzophenone] | (1.0) | 584 |
| [structure: 2-(4-phenylphenyl)-5-(3-methylphenyl)-1,3,4-oxadiazole] | (1.0) | 972 |

Demonstration of the Superiority of Compound of Example 5 to a Mixture of its Component Parts A dry-blended mixture of 0.5 g. Example 5 compound and 100 g. unstabilized cellulose acetate butyrate (CAB) powder of Table I was extruded into 1/16-in. diam. rod, pelletized and pressed into 10-mil film. Samples of this film were exposed to a 280–700-nm. light source until they were brittle when bent approximately 90°. A mixture of 0.25 g. 2-hydroxy-4-methoxybenzophenone, 0.25 g. 2-(4-phenylphenyl)-5-(3-methylphenyl)-1,3,4-oxadiazole and 100 g. CAB was treated similarly and the time-to-embrittlement was determined. The data in Table II show that Compound 6 provides a longer time-to-embrittlement and greater protection against polymer degration (as measured by viscosity change) than a mixture of the component parts.

Table II

Effect of Stabilizer System on Time-To-Embrittlement and Inherent Viscosity (I.V.) of Cellulose Acetate Butyrate Films

| Stabilizer (phr.) | I.V. Initial | I.V. At Embrittlement | Time-To-Embrittlement (Hr.) |
| --- | --- | --- | --- |
| Mixture of 2-hydroxy-4-methoxybenzophenone (0.25) and 2-(4-phenylphenyl)-5-(3-methylphenyl)-1,3,4-oxadiazole (0.25) | 1.39 | 1.15 | 736 |
| Compound of Example 5 | 1.42 | 1.24 | 841 |

The compounds of this invention are highly effective stabilizers for poly(tetramethylene terephthalate) (T4 polyester). To demonstrate this, dry mixture of the stabilizer and granulated polymer were extruded into 1/16-in. dia. rods, pelletized and injection molded into 2½ × ½ × 1/16in. flat bars; these flat bars were exposed to a 280–700 nm. mercury lamp source until a flatwise impact strength of less than 6 was obtained (initial values were all 15).

The results are summarized in Table III.

Table III

Effect of Stabilizers on Time-To-Loss of Impact Strength of Poly(tetramethylene terephthalate), I.V. Approximately 1.2.

| Stabilizer (phr.) | Time-To-Loss of Impact Strength (Hr.) |
| --- | --- |
| None | 70 |
| Example Compound 2, Table I (0.5) | >1700 |
| Example Compound 1, Table I (0.5) | >1700 |
| Example Compound 5, Table I (0.5) | 1050 |
| Example Compound 4, Table I (0.5) | >1700 |

To demonstrate the low volatility of the compounds of this invention relative to existing stabilizers, compositions were prepared consisting of 2 parts stabilizer and 98 parts polymer formulation; the polymer formulation was primarily a mixture comprising per 100 parts of (40 mole percent) isophthalic/(60 mole percent) terephthalic copolyester of 1,4-cyclohexanedimethanol of an I.V. of approximately 0.7, 4 parts of cellulose acetate butyrate, 10 parts of dioctyl phthalate, and 15 parts of $TiO_2$. Extruded pellets of the compositions were ground to a fine powder and then coated onto metal panels. The metal panels with the powder coating were then heated in a oven at 425° F. for 10 minutes and the stabilizer losses were determined. These data (Table IV) clearly show the lower volatility (higher permanance) of the new stabilizers to existing types.

Table IV

Stabilizer Losses From Cured Panels

| Stabilizer | Loss (%) During 425°F./10-min. Curing |
| --- | --- |
| [structure: 2-hydroxy-4-methoxybenzophenone type] | approximately 100% |
| [structure: 2-(4-phenylphenyl)-5-(3-methylphenyl)-1,3,4-oxadiazole] | >99% |

Table IV-continued

Stabilizer Losses From Cured Panels

| Stabilizer | Loss (%) During 425°F./10-min. Curing |
|---|---|
| 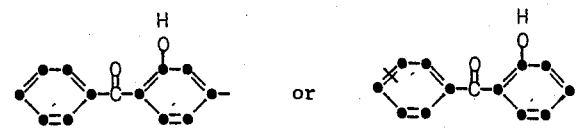 | 41% |
| Example Compound 2 | approximately 0% |
| Example Compound 1 | approximately 0% |

We claim:

1. An organic composition susceptible to ultraviolet light degradation stabilized against such degradation with a stabilizing amount of at least one compound having the formula A and B or A and C wherein A is of the structure:

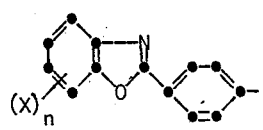 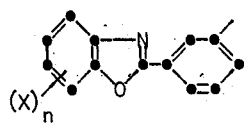

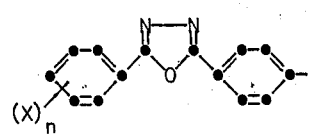 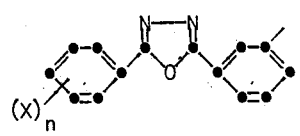

wherein X is meta or para to the heterocyclic ring and may be the following: $C_6H_5$, Cl, Br, lower alkyl and CN, where N = 0-3; B is of the structure:

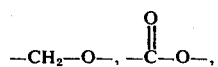

wherein the radical bond is either meta or para to the carbonyl group, A and B being linked through a group selected from

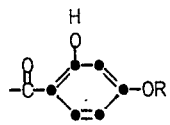

and —O—; and C is of the structure:

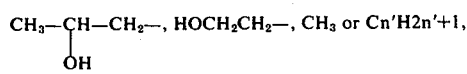

wherein R is $CH_3-CH-CH_2-$, $HOCH_2CH_2-$, $CH_3$ or $C_{n'}H_{2n'+1}$,
     |
     OH where $n' = 2-18$, A and C being linked through a carbon-carbon bond.

2. The composition of claim 1 wherein the polymeric material is cellulose acetate butyrate.

3. The composition of claim 1 wherein said organic composition is polyester.

4. An organic composition susceptible to ultraviolet light degradation stabilized against such degradation according to claim 1 with a stabilizing amount of a compound having the formula

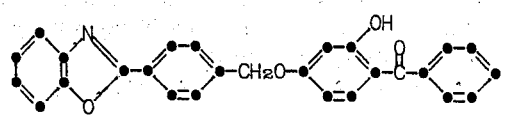

5. An organic composition susceptible to ultraviolet light degradation stabilized against such degradation according to claim 1 with a stabilizing amount of a compound having the formula

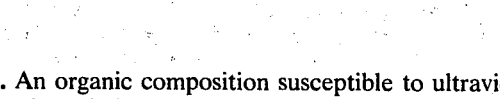

6. An organic composition susceptible to ultraviolet light degradation stabilized against such degradation according to claim 1 with a stabilizing amount of a compound having of the formula

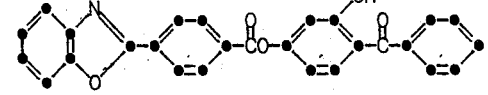

7. An organic composition susceptible to ultraviolet light degradation stabilized against such degradation according to claim 1 with a stabilizing amount of a compound having the formula

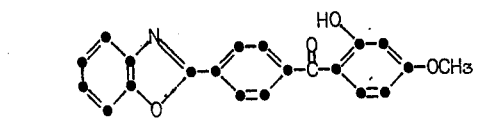

8. An organic composition susceptible to ultraviolet light degradation stabilized against such degradation according to claim 1 with a stabilizing amount of a compound having the formula

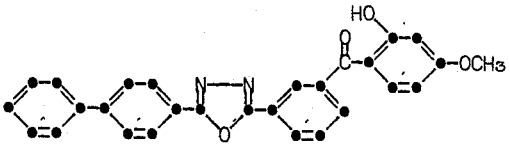

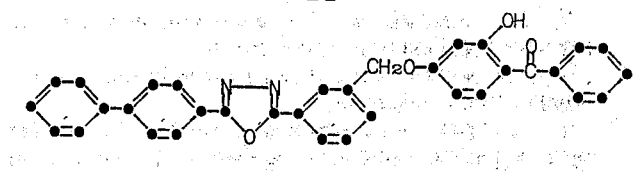

9. An organic composition susceptible to ultraviolet light degradation stabilized against such degradation according to claim 1 with a stabilizing amount of a compound having the formula

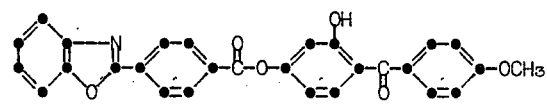

10. An organic composition susceptible to ultraviolet light degradation stabilized against such degradation according to claim 1 with a stabilizing amount of a compound having the formula

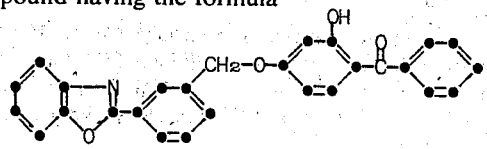

11. An organic composition susceptible to ultraviolet light degradation stabilized against such degradation according to claim 1 with a stabilizing amount of a compound having the formula

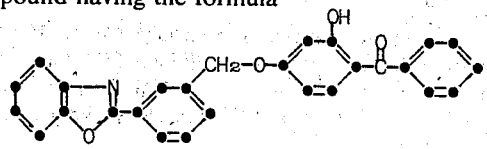

* * * * *